United States Patent
Gregg, Jr.

(10) Patent No.: US 6,319,524 B1
(45) Date of Patent: Nov. 20, 2001

(54) SAW PALMETTO COMPOSITION AND ASSOCIATED METHODS

(75) Inventor: Fred B. Gregg, Jr., Leesburg, FL (US)

(73) Assignee: U.S. Nutraceuticals, Leesburg, FL (US)

( * ) Notice: Subject to any disclaimer, the term of this patent is extended or adjusted under 35 U.S.C. 154(b) by 0 days.

(21) Appl. No.: 09/715,894

(22) Filed: Nov. 17, 2000

Related U.S. Application Data

(60) Provisional application No. 60/166,584, filed on Nov. 19, 1999.

(51) Int. Cl.$^7$ ............................. A61K 35/78; A01N 65/00
(52) U.S. Cl. ................................................ 424/727
(58) Field of Search ............................................. 424/727

(56) References Cited

U.S. PATENT DOCUMENTS

| | | | |
|---|---|---|---|
| 5,932,101 | 8/1999 | Kanel et al. | 210/634 |
| 6,039,950 | * 3/2000 | Khwaja et al. | 424/727 |
| 6,106,720 | 8/2000 | Kanel et al. | 210/634 |

\* cited by examiner

*Primary Examiner*—Herbert J. Lilling
(74) *Attorney, Agent, or Firm*—Allen, Dyer, Milbrath & Gilchrist, P.A.

(57) ABSTRACT

A saw palmetto composition for nutritional supplementation, includes greater than about 0.2% saw palmetto sterols, and essentially no solvent residue. A method of extracting saw palmetto berries includes extracting by contacting ground saw palmetto berries with a substantially continuous flow of carbon dioxide at an extraction pressure of at least about 500 bar, and at a temperature of less than about 80° C. to thereby dissolve saw palmetto compounds in the carbon dioxide.

The method may further include separating the extracted saw palmetto compounds from the carbon dioxide into a plurality of fractions by passing the substantially continuous flow of carbon dioxide after extracting through a plurality of separations. A first separation of the plurality may have a predetermined first separation pressure lower than the extraction pressure, and a temperature sufficient to prevent the carbon dioxide from solidifying, and each subsequent separation may have a lower predetermined pressure than the preceding separation.

43 Claims, 1 Drawing Sheet

SAW PALMETTO COMPOSITION AND ASSOCIATED METHODS

RELATED APPLICATION

This application claims priority from co-pending provisional application Ser. No.60/166584, which was filed on Nov. 19, 1999.

FIELD OF THE INVENTION

The present invention relates to the field of nutritional supplements and, more particularly, to a composition comprising an extract of saw palmetto berries and a method for the extraction of saw palmetto berry components.

BACKGROUND OF THE INVENTION

Saw Palmetto (*Serenoa repens*) is a shrubby palm that grows only in the southeastern United States, and is most prolific on pine flatwoods in peninsular Florida and southern Georgia. The saw palmetto grows a seed stalk (spadix) in late spring, which flowers and then develops a hard green fruit about the size of a small olive. The fruit ripens in the summer, turning shades of yellow, orange and black. The ripe fruit is then harvested by hand during the late summer and early fall. Typical yields in harvestable areas range from a low of 200 lbs. to more than 1000 lbs. of berries per acre.

Saw palmetto berries have been ingested by Native Americans for many centuries. Early in the 20th century, naturopathic physicians in the U.S. began prescribing a tea made from saw palmetto berries as a mild diuretic and for genitourinary problems. It became a popular male tonic, but eventually the therapeutic value of the tea (a water extract) came into question and in the early 1940's it lost both its popularity and its inclusion in the National Formulary. Research in Europe in the 1960's led to the identification of the lipid portion of the berry and its medically active components, including free fatty acids and sterols, also referred to in the art as phytosterols, since they originate in plant tissue.

The therapeutic use of herbs has long been very popular in Europe, but is a relatively recent phenomenon in the U.S. It is instructive, therefore, to review the European experience with herbal medicines over the past few decades. In 1976, Germany defined herbal formulations in the same manner as other drugs, and today about 80% of physicians in general practice prescribe thousands of registered herbal remedies, with most purchases paid for by government health insurance. Other countries within the European Economic Community have similar requirements and restrictions on the manufacture and sale of herbal products, including saw palmetto, with the exception of the United Kingdom (U.K.) and Netherlands, wherein it is treated as a dietary supplement, as in the U.S.

A recent review article in the Journal of American Medical Association (JAMA, November 1998), summarized existing medical evidence regarding the efficacy and safety of saw palmetto berry extract in the treatment of BPH. The study analyzed the results of 18 controlled trials involving 2939 European men between 1965 and 1997. The review concluded that saw palmetto produced a marked reduction in symptoms of BPH when compared to a placebo, and the difference between saw palmetto and the prescription drug finasteride was statistically insignificant. The report further indicated that saw palmetto treatment produced a modest improvement in sexual function, whereas a deterioration was reported with the prescription drug. Also reported was the finding that saw palmetto extract produced fewer adverse side effects, and that its cost of from $3 to $17 per month compared favorably with approximately $67 per month for finasteride.

In 1978 the German Federal Health Agency (now called the Federal Institute for Drugs and Medical Devices), established an expert commission to evaluate the safety and efficacy of herbal remedies, termed phytomedicines (from Greek phyton, plant). This German Commission E actively checks and verifies data on thousands of registered herbal preparations to evaluate their credible utility. Such data include clinical trials, field studies, clinical cases, scientific literature, and medical association experiences. The evaluation process results in the establishment of "reasonable certainty" of the safety and efficacy of the herb being evaluated. The German standard is not equivalent to the standard of "absolute certainty" required by the US Food and Drug Administration (FDA) for drugs. The German approach, however, is much less costly and time consuming than the estimated $500 million expenditure and 12 years of research required to prove the safety and efficacy of a new drug for entry into the U. S. market. In contrast with the U.S., German authorities seem to believe that a reasonable certainty of safety and efficacy is adequate for remedies which have been long-used.

When the German Commission E completes an evaluation, a monograph is prepared for each herbal, with a positive or negative assessment regarding suitability for medicinal use. These monographs now totaling about 300, are published in the *Bundesanzeiger* (Federal Gazette). The monographs describe constituents, range of application, side effects, dosage, use and action of the herb. This listing represents the most accurate information available on the safety and efficacy of herbal medicines. They have recently been translated into English (Blumenthal, 1998).

In the U.K., statutory recognition of herbal remedies increased substantially in 1968 with passage of the Medicines Act. During the 1980's, all U.K. manufacturers were required to make a thorough technical appraisal of their products and to provide evidence on quality, safety and efficacy to the National Department of Health. From a regulatory perspective, however, herbs are still sold as dietary supplements in the U.K., rather than as licensed drugs, as in other European countries. Monographs on aherbal preparations are published in the U.K. by the British Herbal Medicine Association (BHMA). The 1996 *British Herbal Pharmacopoeia* provides monographs for 169 herbs, including saw palmetto.

Saw palmetto was listed in the U.S. Pharmacopeia from 1900 to 1916, and the *National Formulary* from 1925 to 1942. At various times from 1938 to 1990 Food and Drug Acts and Amendments were passed to address the problems of drug safety and effectiveness. Beginning in 1972, the FDA began evaluating over-the-counter drugs, including herbal preparations. In the U.S., however, it is permissible to sell herbal products only if no claims or statements regarding their value in the prevention or treatment of disease are made. In the 1994 Dietary Supplement Health and Education Act (DSHEA), Congress exempted "dietary supplements" including herbal preparations from FDA regulations. The FDA continues to evaluate health claims for herbal preparations, and will approve those claims it considers truthful. For saw palmetto, a frequently-used label in the U.S. includes the claim: "Helps to maintain normal prostate function".

Turning now to the process of extraction, as the saw palmetto berries are harvested, they are usually put into standard citrus boxes, which are then loaded onto flatbed trailers, and transported by truck to drying facilities. The ripe berries contain approximately 66% water and will keep for only a few days without spoiling. The berries are, therefore, dried for several days at about 130°–140° F., and after drying may be stored for several years without deteriorating.

Dried berries are generally bagged and shipped to processing facilities where they are ground into a powder. About 10% of the total powder produced is placed into capsules, generally 500 mg or so, and sold as powdered whole berries. The bulk of the remaining powder is further processed, primarily by chemical extraction facilities in Europe, into a liquid extract which is sold in bulk to companies who fabricate soft gel capsules, also called gelts, for sale to the consumer.

Saw palmetto extract is sold alone (generally in 160 mg. soft gelts), and in a variety of herbal formulations for the treatment of male urological disorders, particularly benign prostatic hyperplasia (BPH) or enlargement of the prostate. As noted, saw palmetto extract is regulated as a prescription drug in Germany, and is used by many patients for treatment of BPH. In the United States, however, partly because of the FDA's lack of regulatory oversight of herbal remedies, these products are used as dietary supplements which may also provide some health benefits. Such dietary supplements, including vitamins and minerals, are viewed by the Food and Nutrition Board of the U.S. Institute of Medicine defines as functional food products with a proven relationship to health maintenance.

As described above, the presently available saw palmetto products are either dried, powdered whole berries, or extracts obtained by extraction with organic solvents such as ethanol or hexane. These processes do not provide a high yield of the lipids which are the preferred components of a saw palmetto herbal product. In addition, the old processes do not allow for the formulation of a saw palmetto extract comprising a predetermined blend of the various lipid fractions, to thereby allow custom formulations to meet customer specifications.

SUMMARY OF THE INVENTION

With the foregoing in mind, the present invention advantageously provides a composition comprising an extract of saw palmetto berries, a method for making the extract, and a method of nutritional supplementation using the composition of the invention.

The composition is primarily intended for oral administration, generally as a gel capsule containing a unit dose. The preferred unit dose contains at least about 160 mg of saw palmetto lipids, and a most preferred unit dose contains about 320 mg of saw palmetto lipids. In addition, in a preferred embodiment of the invention the saw palmetto composition comprises a predetermined blend of saw palmetto phytosterols, saw palmetto triglycerides, and saw palmetto fatty acids, so that a custom blended product may be produced.

The invention also includes a method of extracting saw palmetto berries, wherein the berries are first dried, then ground substantially to a powder, followed by extraction of the ground berries with $CO_2$ under relatively high pressure, and finally separating the extracted compounds from the $CO_2$.

Extracting is accomplished by flowing supercritical $CO_2$ through the powdered saw palmetto berries at an extraction pressure of at least about 500 bar. Those skilled in the art will recognize that a "bar" is a unit of pressure substantially equivalent to one atmosphere, or $10^5$ newton/m². Temperature during extraction is maintained at less than about 80° C. Following extraction, the saw palmetto compounds are separated from the carbon dioxide by decreasing the pressure to a predetermined separation pressure lower than the extraction pressure, and at a temperature sufficient to prevent the carbon dioxide from solidifying. As the pressure is decreased, the dissolving power of the $CO_2$ also decreases and the extracted components come out of solution and are deposited in the separation vessel. Extracting and separating may best be conducted under a substantially continuous flow of carbon dioxide.

BRIEF DESCRIPTION OF THE DRAWINGS

Some of the features, advantages, and benefits of the present invention having been stated, others will become apparent as the description proceeds when taken in conjunction with the accompanying drawing in which.

DETAILED DESCRIPTION OF THE PREFERRED EMBODIMENT

Figure 1:
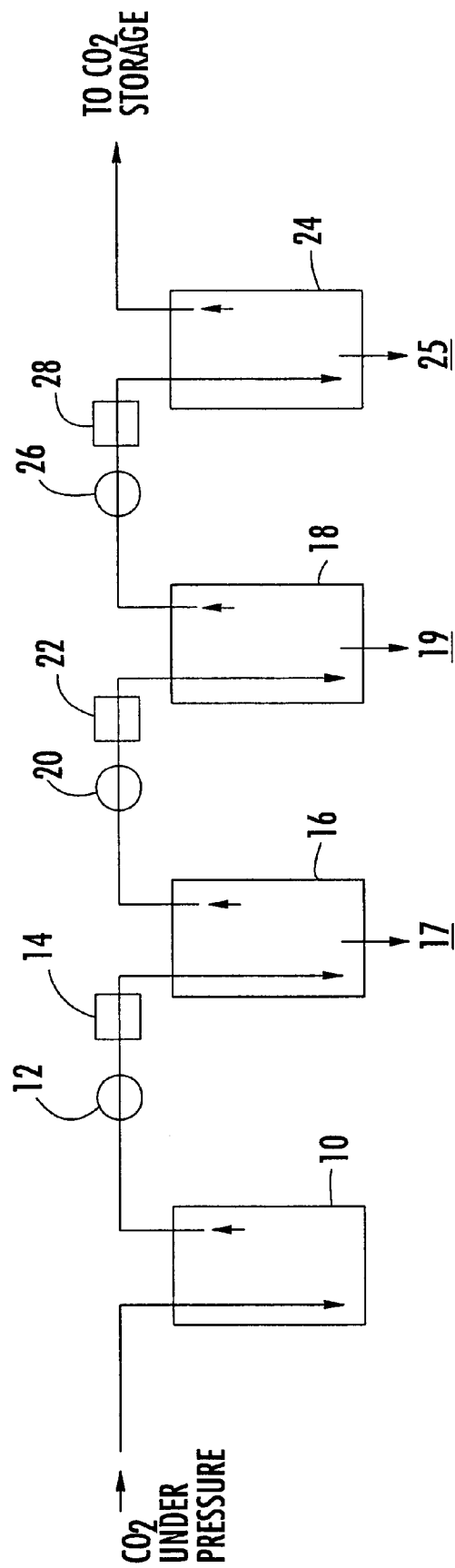
FIG. 1 is a schematic diagram of the saw palmetto extraction process according to an embodiment of the present invention.

The present invention will now be described more fully hereinafter with reference to the accompanying drawings, in which preferred embodiments of the invention are shown. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art.

FIG. 1 illustrates an aspect of the present invention, which includes a process for extraction of saw palmetto berries, a novel composition of saw palmetto berries, comprising at least about 85% saw palmetto lipids, and a method of nutritional supplementation using the disclosed composition. In addition, the composition preferably comprises greater than about 0.2% saw palmetto phytosterols. Because the saw palmetto berries are processed by supercritical fluid extraction with carbon dioxide ($CO_2$), the saw palmetto composition comprises essentially no solvent residue. Those skilled in the art will recognize that the term "lipid" refers to a class of compounds containing long-chain aliphatic hydrocarbons and their derivative acids (fatty acids), alcohols (fatty alcohols), amines, amino alcohols, and aldehydes. Lipids, for example, include triglycerides, waxes, steroids (phytosterols), phospholipids, glycolipids (phytoglycolipids), and sphingolipids.

The present invention includes a method of extracting saw palmetto berries by supercritical fluid extraction using $CO_2$ under high pressure. The method is schematically illustrated in FIG. 1. The method comprises drying the berries, grinding the dried berries, extracting the berries with $CO_2$ under relatively high pressure, and separating the extracted compounds from the $CO_2$. When ripe berries are harvested, they contain approximately 66% water and will keep for only a few days without spoiling. For longer term storage, the harvested berries are dried for several days at 130°–140° F. In the resulting dry state, the berries may be stored for several years without further deteriorating. Dried berries are then bagged and shipped to processing facilities where they are ground to a fineness of about from −40 to about +60 mesh, and preferably into a fine powder.

Extracting is effected in an extractor vessel 10 by contacting the ground saw palmetto berries with $CO_2$ at an extraction pressure of at least about 500 bar, and at a temperature lower than about 80° C. to thereby extract saw palmetto compounds into the $CO_2$. The process includes separating the extracted saw palmetto compounds from the $CO_2$ in a separator vessel into at least a first fraction by collecting the carbon dioxide after extracting and decreasing the pressure to a predetermined first separation pressure lower than the extraction pressure, at a temperature sufficient to prevent the carbon dioxide from solidifying.

In the method, as illustrated in FIG. 1, the $CO_2$ flows into the extraction vessel 10 from a source of high pressure $CO_2$. The extraction vessel is loaded with ground, dried saw palmetto berries, and the $CO_2$ is delivered into the vessel so that it must flow through the loaded product before being discharged from the vessel. As the high pressure $CO_2$ flows through the product, it behaves as a solvent and extracts saw palmetto compounds which are soluble in the fluid. A preferred extraction pressure is about 550 bar, and a preferred first separation pressure is about 250 bar. Extracting is best conducted at a temperature of from about 45° C. to about 80° C., and preferably under a substantially continuous flow of carbon dioxide.

As shown in FIG. 1, from extraction vessel 10, $CO_2$ flows through a pressure reducer 12, with temperature of the $CO_2$ being regulated by a temperature regulator 14, and is conducted into a first separation vessel 16 from which a first fraction 17 is collected.

The method also preferably comprises a second separation having a second separation pressure lower than the first separation pressure to thereby separate a second fraction of dissolved compounds from the carbon dioxide. As seen in FIG. 1, from the first separation vessel 16, the $CO_2$ flows into a second separation vessel 18, having passed through pressure reducer 20 and temperature regulator 22. A second fraction 19 is collected from the second separation vessel. The second separation comprises a separation pressure of about 120 bar.

Additionally, in accordance with some embodiments of the invention, the method may include a third separation having a third separation pressure lower than the second separation pressure to thereby separate a third fraction of extracted compounds from the carbon dioxide. Sequentially, the $CO_2$ flows into a third separation vessel 24, as indicated in FIG. 1, again passing through pressure reducer 26 and temperature regulator 28, and a third fraction 25 is collected. The third separation comprises a separation pressure of about 30 bar. Following the last separation, the $CO_2$ is returned to storage for further use.

Plural separations are most preferably conducted sequentially and in a substantially continuous flow, wherein each subsequent separation comprises a lower predetermined separation pressure. Such sequential separations are also referred to in the industry as cascading separations. Sequential separations allow for separating the extracted saw palmetto compounds from the carbon dioxide into a plurality of fractions. Most preferably, passing the substantially continuous flow of carbon dioxide after extracting through a plurality of separations, results in separation of the extract into several fractions.

In a preferred method, each individual fraction of the resulting plurality of fractions comprises an essentially different fraction of extracted saw palmetto compounds from every other individual fraction. For example, in a preferred method the first fraction comprises essentially a major fraction of saw palmetto sterol compounds, the second fraction comprises essentially a major fraction of saw palmetto triglyceride compounds (fatty acids), and a third fraction comprises essentially a major fraction of saw palmetto fatty alcohol compounds. A greatly advantageous benefit of the present invention, is that the various resulting extraction fractions can be blended in predetermined amounts to thereby prepare a saw palmetto composition comprising desired proportions the various saw palmetto compounds, including phytosterols, triglycerides, and fatty alcohols. This process allows not only for custom blends to meet specific consumer demands, but also for a great degree of standardization of the product.

The invention includes a saw palmetto composition preferably for oral nutritional supplementation. The composition comprises a pharmaceutically acceptable carrier, and is advantageously orally administered as a gel capsule containing a unit dose. A preferred unit dose contains at least about 160 mg of saw palmetto lipids, and a most preferred unit dose contains about 320 mg of saw palmetto lipids. Most advantageously, the saw palmetto composition comprises a predetermined blend of saw palmetto compounds, including phytosterols, triglycerides, and total fatty acids.

The invention also includes a method of providing nutritional supplementation, comprising ingesting a saw palmetto composition having at least about 85% saw palmetto lipids, and preferably greater than about 0.2% saw palmetto sterols. The invention allows for nutritional supplementation ingesting a composition comprising essentially no solvent residue. Ingesting is accomplished by swallowing a capsule unit dose which comprises a pharmaceutically acceptable carrier. A suggested daily dose is about 320 mg of saw palmetto lipids, preferably comprising a relatively high amount of phytosterols. In a preferred unit dose of the present invention, the 320 mg of saw palmetto lipids comprises a predetermined blend of saw palmetto sterols and saw palmetto triglycerides.

Several examples of the method of the present invention for extracting saw palmetto berries are shown in Tables 1–4. Table 1 summarizes the results of extraction of saw palmetto berries at a pressure of at least 500 bar, followed by a sequence of three separations at 200 bar, 120 bar and 30 bar, respectively. As shown in Table 1, in this embodiment of the method, fraction 1, obtained during the first separation at 200 bar, contains twice the concentration of phytosterols found in the whole extract.

Tables 2, 3 and 4 summarize data for an extraction method having two sequential separations. The extraction pressure in each of these examples is at least 500 bar. The first separation pressure, however, increases from a low of 180 bar, as shown in Table 2, to 220 bar shown in Table 3, to a high of 260 bar as shown in Table 4. As shown in Table 2, it should be noted that at a first separation pressure of 180 bar, there is no significant increase in concentration of phytosterols when comparing fraction 1 to the whole extract. When the first separation pressure is increased to 220 bar, as shown in Table 3, recovery of phytosterols in fraction 1 is slightly more than double the concentration of phytosterols in the whole extract. A further increase in the first separation pressure to 260 bar, as noted in Table 4, results in an unexpected ten-fold increase in phytosterol recovery when compared to a whole extract.

Accordingly, the invention has been described in considerable detail with specific reference to these illustrated embodiments. In the specification there has been disclosed a typical preferred embodiment of the invention, and although specific terms are employed, the terms are used in a descriptive sense only and not for purposes of limitation. It will be apparent, however, that various modifications and changes can be made within the spirit and scope of the invention as described in the foregoing specification and as defined in the appended claims.

TABLE 1

SUPERCRITICAL EXTRACTION OF SAW PALMETTO OIL WITH FRACTIONATION INTO A HIGH-STEROL FRACTION

| VESSEL | PRESSURE | TEMP. | FRACTION | YIELD % | % FATTY ACIDS | % STEROLS | % FATTY ALCOHOLS |
|---|---|---|---|---|---|---|---|
| EXTRACTOR | 500 bar | 80° C. | WHOLE EXTRACT | 13.7 | 91.1 | 0.24 | 0.22 |
| SEPARATOR 1 | 200 bar | 65° C. | FRACTION 1 | 1.1 | 81.2 | 0.40 | 0.48 |
| SEPARATOR 2 | 120 bar | 48° C. | FRACTION 2 | 11.1 | 91.8 | 0.12 | 0.15 |
| SEPARATOR 3 | 30 bar | 15° C. | FRACTION 3 | 1.5 | 83.8 | 0.04 | 0.07 |

Fatty Acids by Gas Chromatography.
Phytosterols (total of Campesterol, Stigmasterol and B-Silosterol) by Gas Chromatography.
Fatty Alcohols (total of Hexacosanol, Octacosanol and Triacontanol) by Gas Chromatography.

15

TABLE 2

SUPERCRITICAL EXTRACTION OF SAW PALMETTO OIL WITH FRACTIONATION INTO A HIGH-STEROL FRACTION

| VESSEL | PRESSURE | TEMP. | FRACTION | YIELD % | % FATTY ACIDS | % STEROLS | % FATTY ALCOHOLS |
|---|---|---|---|---|---|---|---|
| EXTRACTOR | 500 bar | 80° C. | WHOLE EXTRACT | 13.2 | 92.2 | 0.252 | N.A. |
| SEPARATOR 1 | 180 bar | 62° C. | FRACTION 1 | 5.6 | 93.4 | 0.196 | 0.22 |
| SEPARATOR 2 | 30 bar | 15° C. | FRACTION 2 | 7.6 | 91.4 | 0.294 | N.A. |

Fatty Acids by Gas Chromatography.
Phytosterols (total of Campesterol, Stigmasterol and B-Silosterol) by Gas Chromatography.
Fatty Alcohols (total of Hexacosanol, Octacosanol and Triacontanoly by Gas Chromatography.

TABLE 3

SUPERCRITICAL EXTRACTION OF SAW PALMETTO OIL WITH FRACTIONATION INTO A HIGH-STEROL FRACTION

| VESSEL | PRESSURE | TEMP. | FRACTION | YIELD % | % FATTY ACIDS | % STEROLS | % FATTY ALCOHOLS |
|---|---|---|---|---|---|---|---|
| EXTRACTOR | 500 bar | 80° C. | WHOLE EXTRACT | 14.1 | 90.6 | 0.24 | 0.25 |
| SEPARATOR 1 | 220 bar | 70° C. | FRACTION 1 | 1.6 | 85.9 | 0.57 | 0.57 |
| SEPARATOR 2 | 30 bar | 15° C. | FRACTION 2 | 12.5 | 92.2 | 0.19 | 0.25 |

Fatty Acids by Gas Chromatography.
Phytosterols (total of Campesterol, Stigmasterol and B-Silosterol) by Gas Chromatography.
Fatty Alcohols (total of Hexacosanol, Octacosanol and Triacontanol) by Gas Chromatography.

TABLE 4

SUPERCRITICAL EXTRACTION OF SAW PALMETTO OIL WITH FRACTIONATION INTO A HIGH-STEROL FRACTION

| VESSEL | PRESSURE | TEMP. | FRACTION | YIELD % | % FATTY ACIDS | % PHYTO-STEROLS | % FATTY ALCOHOLS | TOCO-PHEROLS | B-CAROTENE |
|---|---|---|---|---|---|---|---|---|---|
| EXTRACTOR | 500 bar | 80° C. | WHOLE EXTRACT | 13.8 | N.A. | N.A. | N.A. | N.A. | N.A. |
| SEPARATOR 1 | 260 bar | 75° C. | FRACTION 1 | 0.74 | 59.30 | 2.0 | 1.80 | 103 mg/100 g | 1.18 m IU/100 g |
| SEPARATOR 2 | 30 bar | 15° C. | FRACTION 2 | 13.06 | N.A. | N.A. | N.A. | N.A. | N.A. |

Fatty Acids by Gas Chromatography.
Phytosterols (total of Campesterol, Stigmasterol and B-Silosterol) by Gas Chromatography.
Fatty Alcohols (total of Hexacosanol, Octacosanol and Triacontanol) by Gas Chromatography.
Tocopherols (total alpha, delta, gamma) by High Performance Chromatography plus Tocotrienols by Gas Chromatography.
Beta Carotene by High Performance Gas Chromatography.

That which is claimed:

1. A method of extracting saw palmetto berries, comprising:
   extracting by contacting ground saw palmetto berries with a substantially continuous flow of carbon dioxide at an extraction pressure of at least about 500 bar, and at a temperature of less than about 80° C. to thereby dissolve saw palmetto compounds in the carbon dioxide; and
   separating the extracted saw palmetto compounds from the carbon dioxide into a plurality of fractions by passing the substantially continuous flow of carbon dioxide after extracting through a plurality of separations, a first separation of the plurality having a predetermined first separation pressure lower than the extraction pressure, and a temperature sufficient to prevent the carbon dioxide from solidifying, and each subsequent separation having a lower predetermined pressure than the preceding separation.

2. The method of claim 1, wherein the first separation comprises a pressure of from about 160 bar to about 350 bar at a temperature of from about 35° C. to about 85° C.

3. The method of claim 1, wherein a second separation of the plurality of separations comprises a pressure of from about 50 bar to about 200 bar at a temperature of from about 20° C. to about 70° C.

4. The method of claim 1, wherein a third separation of the plurality of separations comprises a pressure of from about 30 bar to about 80 bar at a temperature of from about 12° C. to about 30° C.

5. The method of claim 1, wherein separating comprises three sequential separations including a first separation carried out from about 160 bar to about 350 bar at a temperature of from about 35° C. to about 85° C., a second separation carried out from about 50 bar to about 200 bar at a temperature of from about 20° C. to about 70° C., and a third separation carried out from about 30 bar to about 80 bar at a temperature of from about 12° C. to about 30° C.

6. The method of claim 1, wherein separating comprises three sequential separations including a first separation carried out from about 180 bar to about 300 bar at a temperature of from about 40° C. to about 80° C., a second separation carried out from about 70 bar to about 180 bar at a temperature of from about 28° C. to about 65° C., and a third separation carried out from about 30 bar to about 60 bar at a temperature of from about 12° C. to about 24° C.

7. The method of claim 1, wherein separating comprises three sequential separations including a first separation carried out from about 220 bar to about 280 bar at a temperature of from about 45° C. to about 65° C., a second separation carried out from about 80 bar to about 150 bar at a temperature of from about 30° C. to about 45° C., and a third separation carried out from about 30 bar to about 50 bar at a temperature of from about 12° C. to about 20° C.

8. The method of claim 1, wherein separating comprises two sequential separations including a first separation carried out from about 160 bar to about 350 bar at a temperature of from about 35° C. to about 85° C., and a second separation carried out from about 30 bar to about 200 bar at a temperature of from about 12° C. to about 70° C.

9. The method of claim 1, wherein separating comprises two sequential separations including a first separation carried out from about 180 bar to about 300 bar at a temperature of from about 40° C. to about 80° C., and a second separation carried out from about 80 bar to about 160 bar at a temperature of from about 12° C. to about 50° C.

10. The method of claim 1, wherein separating comprises two sequential separations including a first separation car-ried out from about 220 bar to about 280 bar at a temperature of from about 45° C. to about 65° C., and a second separation carried out from about 30 bar to about 100 bar at a temperature of from about 12° C. to about 35° C.

11. The method of claim 1, wherein the ground saw palmetto berries are ground substantially to a fineness of about from −40 to about +60 mesh.

12. The method of claim 1, wherein the ground saw palmetto berries are ground substantially into a powder.

13. The method of claim 1, wherein the extraction pressure is at least about 550 bar.

14. The method of claim 1, wherein extracting is conducted at a temperature of from about 45° C. to about 80° C.

15. The method of claim 1, wherein each individual fraction of the plurality of fractions comprises a different fraction of saw palmetto compounds from every other individual fraction of the plurality of fractions.

16. The method of claim 1, wherein a first fraction of the plurality of fractions comprises a major fraction of saw palmetto sterol compounds.

17. The method of claim 1, wherein a second fraction of the plurality of fractions comprises a major fraction of saw palmetto triglyceride compounds.

18. The method of claim 1, wherein a third fraction of the plurality of fractions comprises a major fraction of saw palmetto fatty acid compounds.

19. The method of claim 1, further comprising blending predetermined amounts of individual fractions of the plurality of fractions to thereby prepare a saw palmetto composition comprising desired proportions of saw palmetto compounds.

20. A method of extracting saw palmetto berries, comprising:
   drying the berries;
   grinding the dried berries;
   extracting by contacting the ground saw palmetto berries with carbon dioxide at an extraction pressure of at least about 500 bar, and at a temperature of less than about 80° C. to thereby dissolve saw palmetto compounds in the carbon dioxide; and
   separating the extracted saw palmetto compounds from the carbon dioxide into at least a first fraction by collecting the carbon dioxide after extracting and decreasing the pressure to a predetermined first separation pressure lower than the extraction pressure, and at a temperature sufficient to prevent the carbon dioxide from solidifying.

21. The method of claim 20, wherein the first separation comprises a pressure of from about 160 bar to about 350 bar at a temperature of from about 35° C. to about 85° C.

22. The method of claim 20, wherein a second separation of the plurality of separations comprises a pressure of from about 50 bar to about 200 bar at a temperature of from about 20° C. to about 70° C.

23. The method of claim 20, wherein a third separation of the plurality of separations comprises a pressure of from about 30 bar to about 80 bar at a temperature of from about 12° C. to about 30° C.

24. The method of claim 20, wherein separating comprises three sequential separations including a first separation carried out from about 160 bar to about 350 bar at a temperature of from about 35° C. to about 85° C., a second separation carried out from about 50 bar to about 200 bar at a temperature of from about 20° C. to about 70° C., and a third separation carried out from about 30 bar to about 80 bar at a temperature of from about 12° C. to about 30° C.

25. The method of claim 20, wherein separating comprises three sequential separations including a first separation carried out from about 180 bar to about 300 bar at a temperature of from about 40° C. to about 80° C., a second separation carried out from about 70 bar to about 180 bar at a temperature of from about 28° C. to about 65° C., and a third separation carried out from about 30 bar to about 60 bar at a temperature of from about 12° C. to about 24° C.

26. The method of claim 20, wherein separating comprises three sequential separations including a first separation carried out from about 220 bar to about 280 bar at a temperature of from about 45° C. to about 65° C., a second separation carried out from about 80 bar to about 150 bar at a temperature of from about 30° C. to about 45° C., and a third separation carried out from about 30 bar to about 50 bar at a temperature of from about 12° C. to about 20° C.

27. The method of claim 20, wherein separating comprises two sequential separations including a first separation carried out from about 160 bar to about 350 bar at a temperature of from about 35° C. to about 85° C., and a second separation carried out from about 30 bar to about 200 bar at a temperature of from about 12° C. to about 70° C.

28. The method of claim 20, wherein separating comprises two sequential separations including a first separation carried out from about 180 bar to about 300 bar at a temperature of from about 40° C. to about 80° C., and a second separation carried out from about 80 bar to about 160 bar at a temperature of from about 12° C. to about 50° C.

29. The method of claim 20, wherein separating comprises two sequential separations including a first separation carried out from about 220 bar to about 280 bar at a temperature of from about 45° C. to about 65° C., and a second separation carried out from about 30 bar to about 100 bar at a temperature of from about 12° C. to about 35° C.

30. The method of claim 20, wherein grinding comprises grinding the dried saw palmetto berries substantially to a fineness of about from −40 to about +60 mesh.

31. The method of claim 20, wherein grinding comprises grinding the dried saw palmetto berries substantially into a powder.

32. The method of claim 20, wherein the extraction pressure is at least about 550 bar.

33. The method of claim 20, wherein the first separation pressure is about 250 bar.

34. The method of claim 20, wherein separating comprises a second separation having a second separation pressure lower than the first separation pressure to thereby separate a second fraction of extracted compounds from the carbon dioxide.

35. The method of claim 34, wherein the second separation pressure is about 120 bar.

36. The method of claim 34, wherein separating comprises a third separation having a third separation pressure lower than the second separation pressure to thereby separate a third fraction of extracted compounds from the carbon dioxide.

37. The method of claim 36, wherein the third separation pressure is about 30 bar.

38. The method of claim 20, wherein extracting is conducted at a temperature of from about 45° C. to about 80° C.

39. The method of claim 20, further comprising a substantially continuous flow of carbon dioxide.

40. The method of claim 20, wherein extracting comprises a substantially continuous flow of carbon dioxide.

41. The method of claim 20, wherein separating comprises a substantially continuous flow of carbon dioxide.

42. The method of claim 20, wherein separating comprises a plurality of separations.

43. The method of claim 42, wherein each subsequent separation of the plurality of separations comprises a lower predetermined separation pressure.

\* \* \* \* \*

UNITED STATES PATENT AND TRADEMARK OFFICE
CERTIFICATE OF CORRECTION

PATENT NO. : 6,319,524 B1
DATED : November 20, 2001
INVENTOR(S) : Fred B. Gregg, Jr.

It is certified that error appears in the above-identified patent and that said Letters Patent is hereby corrected as shown below:

Title page,
Item [74], delete "*Attorney, Agent, or Firm*-Allen, Dyer, Milbrath & Gilchrist, P.A."
insert -- *Attorney, Agent, or Firm*-Allen, Dyer, Doppelt, Milbrath & Gilchrist, P.A. --

Column 2,
Line 9, delete "This German Commission E" insert -- This German Commission --
Line 26, delete "This German Commission E" insert -- This German Commission --
Line 45, delete "aherbal" insert -- herbal --

Column 3,
Line 27, delete "Medicine defines as" insert -- Medicine as --

Column 6,
Line 7, delete "desired proportions the various" insert -- desired proportions of the various --

Column 7,
Line 30, delete "Triacontanoly by Gas Chromatography." insert -- Triacontanol) by Gas Chromatography. --

Signed and Sealed this

Twenty-third Day of April, 2002

*Attest:*

JAMES E. ROGAN
*Attesting Officer*     *Director of the United States Patent and Trademark Office*